United States Patent [19]

Alig et al.

[11] 4,026,922
[45] May 31, 1977

[54] D-HOMO-PREGNENE STEROIDS

[76] Inventors: Leo Alig, 76 Heidenlochstrasse, Liestal; Andor Furst, 14 Magnolienpark, Basel; Marcel Muller, 10 Quellenweg, Frenkendorf, all of Switzerland; Ulrich Kerb, 8 Waitzstrasse; Rudolf Wiechert, 5 Petzowerstrasse, both of Berlin, Germany

[22] Filed: Oct. 2, 1975

[21] Appl. No.: 619,065

[30] Foreign Application Priority Data

Oct. 7, 1974  Switzerland ............... 13424/74
Dec. 2, 1974  Switzerland ............... 15950/74
Mar. 13, 1975  Switzerland ............... 3195/75

[52] U.S. Cl. ............... 260/488 B; 260/326.33; 260/326.5 C; 260/327 M; 260/340.9; 260/345.9; 260/348 A; 260/348 C; 260/408; 260/410; 260/456 R; 260/468 R; 260/476 C; 260/486 H; 260/491; 260/586 E; 260/600 R; 424/305; 424/308; 424/311; 424/312; 24/331

[51] Int. Cl.² ............... C07J 63/00

[58] Field of Search .......... 260/488 B, 586 E, 410, 260/408, 476 C, 468 R, 486 R, 486 H

[56] References Cited

UNITED STATES PATENTS 2,860,158  11/1958  Clinton ................ 260/488 B
3,076,023  1/1963   Kaspar et al. ........ 260/488 B

*Primary Examiner*—Vivian Garner
*Attorney, Agent, or Firm*—Samuel L. Welt; George M. Gould

[57] ABSTRACT

The present disclosure relates to novel D-homo-pregnene steroids useful as progestational agents.

35 Claims, No Drawings

D-HOMO-PREGNENE STEROIDS

DESCRIPTION OF THE INVENTION

The D-homosteroids provided by the present invention have the following general formula

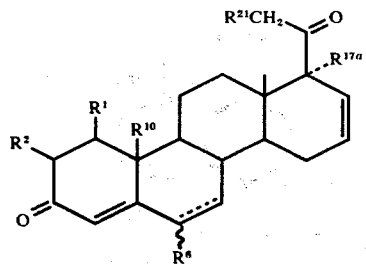

wherein $R^1$ and $R^2$ each represent a hydrogen atom or $R^1$ and $R^2$ together represent a 1α, 2α-methylene group or a carbon-carbon bond; $R^6$ represents a hydrogen, fluorine or chlorine atom or the methyl group; $R^{17a}$ represents a hydroxy, acyloxy, alkoxy or lower alkyl group; $R^{10}$ represents the methyl group or, when $R^1$ and $R^2$ each represent a hydrogen atom, $R^{10}$ can also represent a hydrogen atom; $R^{21}$ represents a hydrogen, fluorine or chlorine atom and the broken line in the 6,7-position denotes an optional carbon-carbon bond.

An acyloxy group can be derived from a saturated or unsaturated aliphatic caboxylic acid, a cycloaliphatic carboxylic acid, an araliphatic carboxylic acid or an aromatic carboxylic acid, said acids preferably containing up to 15 carbon atoms. Examples of such acids are formic acid, acetic acid, pivalic acid, propionic acid, butyric acid, caproic acid, oenanthic acid, undecylenic acid, oleic acid, cyclopentylpropionic acid, cyclohexylpropionic acid, phenylacetic acid and benzoic acid. Alkanoyloxy groups containing from 1 to 7 carbon atoms are especially preferred. Alkoxy groups can be straight-chain or branced-chain groups and preferably contain up to 15 carbon atoms. Lower alkoxy groups are especially preferred, particularly the methoxy and ethoxy groups. Lower alkyl groups preferably contain from 1 to 4 carbon atoms, especially the methyl and ethyl groups.

In 6,7-saturated D-homosteroids of formula I, a substitutent in the 6-position can have α- or β-configuration, the α-isomer being preferred.

According to the process provided by the present invention, the D-homosteroids of formula I are manufactured by a. oxidizing the 3-hydroxy-Δ⁵-grouping in a D-homosteroid of the general formula

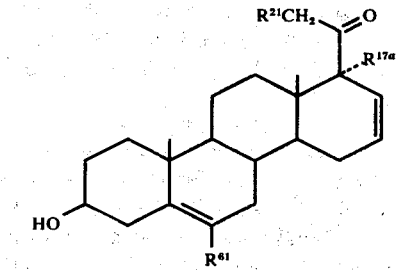

wherein $R^{61}$ represents a hydrogen atom or the methyl group and $R^{17a}$ and $R^{21}$ have the significance given earlier, to the 3-keto-$\Delta^4$-, 3-keto-$\Delta^{4,6}$- or 3-keto-$\Delta^{1,4,6}$-grouping, or b. dehydrogenating a D-homosteroid of the general formula

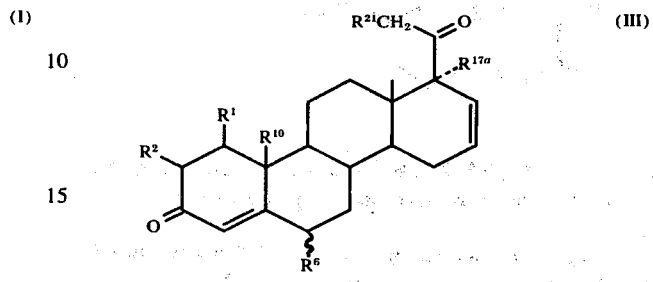

wherein $R^1$, $R^2$, $R^6$, $R^{10}$, $R^{17a}$ and $R^{21}$ have the significance given earlier, in the 1,2-position and/or 6,7-position when $R^1$ and $R^2$ each represent a hydrogen atom and $R^{10}$ represents the methyl group, or in the 6,7-position when $R^1$ and $R^2$ together represent a 1α,2α-methylene group or a carbon-carbon bond of $R^{10}$ represents a hydrogen atom, or dehydrogenating in the 1,2-position a 6-dehydro derivative of a D-homosteroid of formula III in which $R^1$ and $R^2$ each represent a hydrogen atom and $R^{10}$ represents the methyl group, or c. fluorinating or chlorinating a D-homosteroid of the general formula

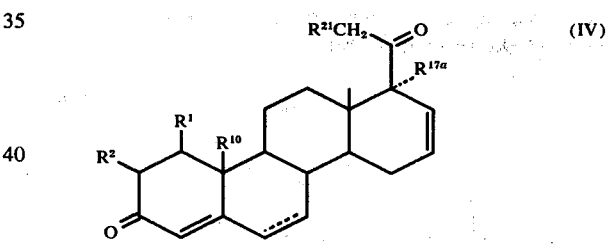

wherein $R^1$, $R^2$, $R^{10}$, $R^{17a}$, $R^{21}$ and the broken line in the 6,7-position have the significance given earlier, in the 6-position and, if desired, isomerising a 6α-isomer, or d. methylating a D-homosteroid of the general formula

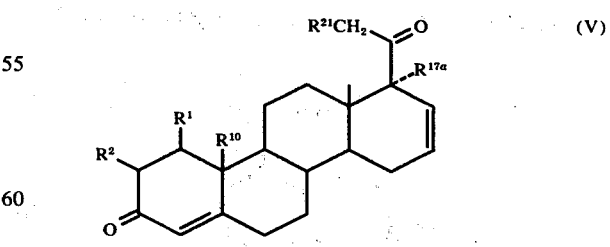

wherein $R^1$, $R^2$, $R^{10}$, $R^{17a}$ and $R^{21}$ have the significance given earlier, in the 6-position, or e. acylating the hydroxy group in a D-homosteroid of the general formula

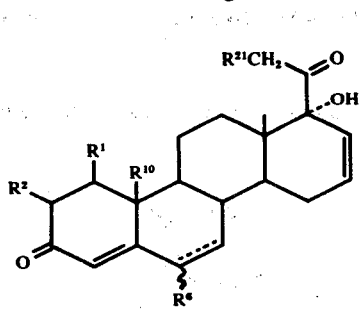

wherein $R^1$, $R^2$, $R^6$, $R^{10}$, $R^{21}$ and the broken line in the 6,7-position have the significance given earlier
or f. adding a methylene group to the 1,2-double bond of a D-homosteroid of the general formula

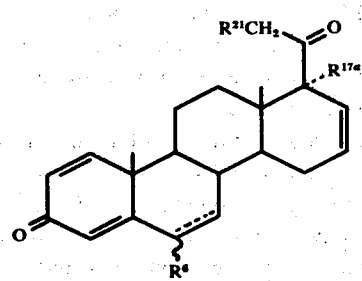

wherein $R^6$, $R^{17a}$, $R^{21}$ and the broken line in the 6,7-position have the significance given earlier,
or g. replacing the 21-hydroxy group in a D-homosteroid of the general formula

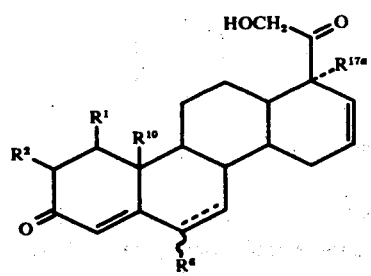

wherein $R^1$, $R^2$, $R^6$, $R^{10}$, $R^{17a}$ and the broken line in the 6,7-position have the significance given earlier, by a fluorine or chlorine atom,
or h. subjecting a D-homosteroid of the general formula

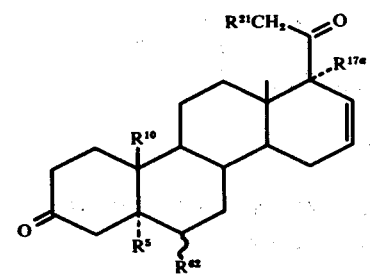

wherein $R^{10}$, $R^{17a}$ and $R^{21}$ and the significance given earlier, $R^5$ represents a fluorine, chlorine or bromine atom or a hydroxy group and $R^{62}$ represents a fluorine, chlorine or bromine atom or the methyl group, to a $HR^5$-cleavage,
or i. hydrolysing a D-homosteroid of the general formula

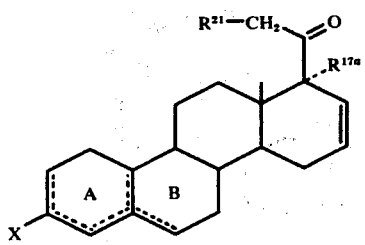

wherein $R^{17a}$ and $R^{21}$ have the significance given earlier, X represents an organic grouping joined to the ring via a nitrogen, oxygen or sulphur atom and at least one of the bonds denoted by the broken lines in rings A and B is present,
with the formation of a $\Delta^4$-3-ketone.

The oxidation of a D-homosteroid of formula II in accordance with embodiment (a) of the present process can be carried out according to the Oppenauer procedure (e.g. by means of aluminium isoporopylate), or using an oxidising agent such as chromium trioxide (e.g. Jones' reagent), or according to the Pfitzner-Moffatt procedure using dimethyl sulphoxide/dicyclohexylcarbodiimide (the initially obtained $\Delta^5$-3-ketone requiring subsequent isomerisation to the $\Delta^4$-3-ketone), or using pyridine/sulphur trioxide. When the previously mentioned oxidising agents are used, there is obtained a 3-keto-$\Delta^4$-grouping. When an oxidising agent such as bromine/lithium bromide/lithium carbonate in dimethylformamide is used or when the oxidation is carried out according to the Oppenauer procedure in the presence of benzoquinone, the oxidation yields a 3-keto-$\Delta^{4,6}$-grouping. A suitable agent for the oxidation to a 3-keto-$\Delta^{1,4,6}$-steroid is, for example, 2,3-dichloro-5,6-dicyano-benzoquinone.

The 1,2-dehydrogenation of a D-homosteroid of formula III in accordance with embodiment (b) of the present process can be carried out in a manner known per se; for example, in a microbiological manner or by means of a dehydrogenation agent such as selenium dioxide, 2,3-dichloro-5,6-dicyanobenzoquinone, chloranil, thallium triacetate or lead tetraacetate. Suitable microorganisms for the 1,2-dehydrogenation are, for example, Schizomycetes, especially those of the genera Arthrobacter (e.g. A simplex ATCC 6946), Bacillus (e.g. B. lentus ATCC 13805 and B. sphaericua ATTCC 7055), Pseudomonas (e.g. P. aeruginosa IFO 3505), Flavobacterium (e,g, F. flavescens IFO 3058), Lactobacillus (e.g. L. brevis IFO 3345) and Nocardia (e.g. N. opaca ATCC 4276).

The introduction of a $\Delta^6$-double bond into a D-homosteroid of formula III can be carried out, for example, using a substituted benzoquinone such as chloranil [see J. Am. Chem. Soc. 82, 4293 (1960); 81, 5951 (1959)] or using 2,3-dichloro-5,6-dicyano-benzoquinone or using manganese dioxide [see J. Am. Chem. Soc. 75, 5932 (1953)].

When 2,3-dichloro-5,6-dicyanobenzoquinone or chloranil is used, a 1,4,6-trisdehydro-D-homosteroid can be obtained directly from a compound of formula III in which R¹ and R² both represent a hydrogen atom.

The halogenation of a D-homosteroid of formula IV in the 6-position in accordance with embodiment (c) of the present process is preferably carried out by converting a 6,7-saturated D-homosteroid of formula IV into a 3-enol ester or 3-enol ether (e.g. the 3-enol acetate) and then reacting said enol ester or enol ether with chlorine [see J. Am. Chem. Soc. 82, 1230 (1960)], with an appropriate N-haloimide [see J. Am. Chem. Soc. 82, 1230 (1960); 77, 3827 (1955)] or with perchloryl fluoride [see J. Am. Chem. Soc. 81, 5259 (1959); Chem. and Ind. 1959, 1317]. Further, trifluoromethyl hypofluorite may be used as a fluorinating agent.

A further possibility for the halogenation in the 6-position consists in converting a 4,6-bisdehydro- or 1,4,6-trisdehydro-D-homosteroid of formula IV into a 6α,7α-oxide (e.g. by treatment with a peracid such as perphthalic acid, m-chloroperbenzoic acid or p-nitroperbenzoic acid), treating the 6α,7α-oxide with an appropriate dimethylacetamide hydrohalide and cleaving off water from the resulting 7-hydroxy-6-halosteroid with elimination of the 7-hydroxy group and introduction of a 6,7-double bond.

Further, the chlorination can also be carried out by means of chromyl chloride in methylene chloride or an ether.

A further method for the halogenation in the 6-position consists in treating an aforementioned 6α,7α-epoxide with an appropriate lithium halide in glacial acetic acid, converting the resulting 6β-chloro,7α-hydroxy intermediate into a corresponding 7α-alkyl- or aryl-sulphonic acid ester and eliminating the ester group by heating with a base to give a 6-chloro-Δ⁶-D-homosteroid.

Insofar as isomer mixtures (i.e. mixtures of 6α- and 6β-halo-D-Homosteroids) are formed in the previously described halogenation procedures, these mixtures can be separated into the pure isomers according to known methods such as chromatography.

The isomerisation of 6β-halo-D-homosteroid to a 6α-halo-D-homosteroid can be carried out by treatment with an acid, especially a mineral acid such as hydrochloric acid or hydrobromic acid, in a solvent (e.g. dioxane or glacial acetic acid).

The methylation of a D-homosteroid of formula V according to embodiment (d) of the present process can be carried out, for example, by converting a D-homosteroid of formula V into a 3-enol ether (e.g. by treatment with an orthoformic acid ester such as ethyl orthoformate in the presence of an acid such as p-toluenesulphonic acid, if desired with the addition of the corresponding alcohol, or by treatment with a dialkoxypropane such as 2,2-dimethoxypropane in methanol/dimethylformamide in the presence of p-toluenesulphonic acid) and reacting the resulting enol ether with a tetrahalomethane (e.g. tetrabromoethane, dibromodichloromethane or bromotrichloromethane) to give a trihalomethyl-Δ⁴-3-ketone. The trihalomethyl-Δ⁴-3-ketone can then be dehydrohalogenated with a base such as collidine to give a dihalomethylene-Δ⁴-3-ketone which, in turn, can be converted into a desired 6α-methyl-Δ⁴- 3-ketone by catalytic hydrogenation under mild conditions (e.g. in the presence of a palladium/strontium carbonate catalyst).

In the case of D-homosteroids of formula V in which R¹ and R² both represent a hydrogen atom, an advantageous methylation procedure consists in converting such a D-homosteroid of formula V into a 3-enol ether in the manner described earlier, reacting the enol ether in a manner known per se to give a corresponding 6-formyl derivative, reducing the formyl group to the hydroxymethyl group with sodium borohydride and finally dehydrating the reduction product with cleavage of the enol ether to give a D-homosteroid intermediate of the general formula

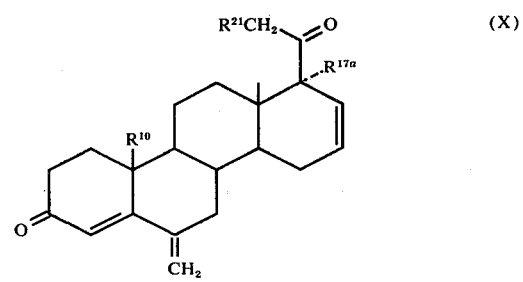

(X)

wherein R¹⁰, R²¹ and R¹⁷ᵃ have the significance given earlier.

6-Methylene intermediates can also be obtained by converting a D-homosteroid of formula V into a 3-enamine (e.g. the 3-pyrrolidinium-enamine), hydroxymethylating the 3-enamine with formaldehyde and cleaving water from the hydroxymethylation product by means of an acid such as p-toluenesulphonic acid.

The isomerisation of a 6-methylene intermediate to give a 6-methyl-Δ⁶-D-homosteroid can be carried out in a manner known per se; for example, catalytically. Suitable isomerisation catalysts are, for example, metal catalysts such as those which are also used in hydrogenations, especially palladium in ethanol. In this isomerisation, a hydrogen donator such as cyclohexene is expediently added as an activator for the catalyst. Undesired side-reactions such as hydrogenation by the hydrogen donator can be avoided by buffering the isomerisation mixture. Moreover, the 6-methylene intermediates can be hydrogenated to the corresponding 6-methyl-D-homosteroids in the usual manner by means of known hydrogenation catalysts.

The acylation of the 17a- hydroxy group in a D-homosteroid of formula VI in accordance with embodiment (e) of the present process can be carried out in a manner known per se by treatment with a reactive acid derivative such as an acyl halide or anhydride in the presence of p-N,N-dimethylaminopyridine.

The 1,2-methylenation of a D-homosteroid of formula VII according to embodiment (f) of the present process can be carried out according to methods known per se for the addition of a methylene group to a double bond with formation of a cyclopropyl-condensed ring system. It can be carried out, for example, according to the Corey procedure by means of dimethylsulphoxonium methylide. In this procedure, a D-homosteroid of formula VII is reacted, for example, with a solution prepared from trimethylsulphoxonium iodide and sodium hydride in dimethylsulphoxide. The 1,2-methylenation can also be carried out, for example, by attachment of diazomethane and thermal decomposition of the intermediate obtained.

The replacement of the 21-hydroxy group by a chlorine or fluorine atom in a D-homosteroid of formula VIII in accordance with embodiment (g) of the present process can be carried out via the mesylate or tosylate by reaction with an appropriate alkali metal halide such as sodium fluoride, sodium chloride or lithium chloride or with carbon tetrachloride and triphenyl phosphine in dimethylformamide.

The $HR^5$-cleavage from a D-homosteroid of formula IX in accordance with embodiment (h) of the present process, which represents a dehydration or a dehydrohalogenation according to the nature of the $R^5$ substituent, can be carried out in a manner known per se. The dehydration can be carried out by treatment with an acid (e.g. a mineral acid such as hydrochloric acid) or with a base. The dehydrohalogenation can likewise be carried out by means of an acid or base (e.g. an organic base such as pyridine).

The hydrolysis of the grouping denoted by X in the 3-position of a D-homosteroid of formula XI in accordance with embodiment (i) of the present process can be carried out in a manner known per se with an acid (e.g. a mineral acid such as hydrochloric acid or a carboxylic acid such as oxalic acid). An especially suitable medium in which to carry out the hydrolysis is an alcoholic or aqueous-alcoholic solution (e.g. methanol or methanol/water) which may contain further solvent (e.g. chloroform.

Examples of D-homosteroids of formula XI are those in which X together with double bond(s) in the rings A and/or B represents a 3-alkoxy-(e.g. methoxy)-$\Delta^{2,5(10)}$-, a 3-alkylthio-(e.g. methylthio)-$\Delta^{2,5(10)}$-, a 3-(secondary amino)-(e.g. pyrrolidino)-$\Delta^{2,5(10)}$-, a 3,3-alkylenedioxy-(e.g. ethylenedioxy)-$\Delta^{5(10)}$-, $\Delta^4$- or $\Delta^5$- or a 3,3-alkylenedithio-(e.g. ethylenedithio)-$\Delta^{5(10)}$, $\Delta^4$- or $\Delta^5$- grouping.

A preferred class of D-homosteroids of formula I comprises those in which $R^1$ and $R^2$ each represent a hydrogen atom or $R^1$ and $R^2$ together represent a $1\alpha$, $2\alpha$-methylene group or a carbon-carbon bond; $R^6$ represents a hydrogen, fluorine or chlorine atom or the methyl group; $R^{17a}$ represents a hydroxy, acyloxy or alkoxy group; $R^{10}$ represents the methyl group or, when $R^1$ and $R^2$ each represent a hydrogen atom, $R^{10}$ can also represent a hydrogen atom; $R^{21}$ represents a hydrogen, fluorine or chlorine atom and the broken line in the 6,7-position denotes an optional carbon-carbon bond.

Further, there are preferred D-homosteroids of formula I in which $R^1$ and $R^2$ each represent a hydrogen atom, $R^6$ represents a hydrogen or chlorine atom or the methyl group, $R^{17a}$ represents a hydroxy or $C_{1-7}$-alkanoyloxy group and $R^{21}$ represents a hydrogen or chlorine atom, especially those in which $R^1$, $R^2$ and $R^{21}$ each represent a hydrogen atom, $R^6$ represents a hydrogen or chlorine atom or the methyl group, $R^{10}$ represents the methyl group and $R^{17a}$ represents a $C_{1-7}$-alkanoyloxy group and in which a double bond is present in the 6,7-position.

Examples of D-homosteroids of formula I are:

17aα-acetoxy-6α-chloro-D-homo-4,16-pregnadiene-3,20-dione,

17aα-acetoxy-6α-fluoro-D-homo-4,16-pregnadiene-3,20-dione,

17aα-acetoxy-6α-methyl-D-homo-4,16-pregnadiene-3,20-dione,

17aα-acetoxy-D-homo-4,16-pregnadiene-3,20-dione,

17aα-acetoxy-6α-chloro-D-homo-1,4,16-pregnatriene-3,20-dione,

17aα-acetoxy-6α-fluoro-D-homo-1,4,16-pregnatriene-3,20-dione,

17aα-acetoxy-6α-methyl-D-homo-1,4,16-pregnatriene-3,20-dione,

17aα-acetoxy-D-homo-1,4,16-pregnatriene-3,20-dione,

17aα-acetoxy-6-chloro-D-homo-4,6,16-pregnatriene-3,20-dione,

17aα-acetoxy-6-fluoro-D-homo-4,6,16-pregnatriene-3,20-dione,

17aα-acetoxy-6-methyl-D-homo-4,6,16-pregnatriene-3,20-dione,

17aα-acetoxy-D-homo-4,6,16-pregnatriene-3,20-dione,

17aα-acetoxy-6-chloro-D-homo-1,4,6,16-pregnatetraene-3,20-dione,

17aα-acetoxy-6-fluoro-D-homo-1,4,6,16-pregnatetraene-3,20-dione,

17aα-acetoxy-6-methyl-D-homo-1,4,6,16-pregnatetraene-3,20-dione,

17aα-acetoxy-D-homo-1,4,6,16-pregnatetraene-3,20-dione,

17aα-acetoxy-6α-chloro-1α, 2α-methylene-D-homo-4,16-pregnadiene-3,20-dione,

17aα-acetoxy-6α-fluoro-1α, 2α-methylene-D-homo-4,16-pregnadiene-3,20-dione,

17aα-acetoxy-6α-methyl-1α, 2α-methylene-D-homo-4,16-pregnadiene-3,20-dione,

17aα-acetoxy-1α, 2α-methylene-D-homo-4,16-pregnadiene-3,20-dione,

17aα-acetoxy-6-chloro-1α, 2α-methylene-D-homo-4,6,16-pregnatriene-3,20-dione,

17aα-acetoxy-6-fluoro-1α, 2α-methylene-D-homo-4,6,16-pregnatriene-3,20-dione,

17aα-acetoxy-6-methyl-1α, 2α-methylene-D-homo-4,6,16-pregnatriene-3,20-dione,

17aα-acetoxy-1α, 2α-methylene-D-homo-4,6,16-pregnatriene-3,20-dione,

6α-chloro-17a-methyl-D-homo-4,16-pregnadiene-3,20-dione,

6α-fluoro-17a-methyl-D-homo-4,16-pregnadiene-3,20-dione,

6α, 17aα-dimethyl-D-homo-4,16-pregnadiene-3,20-dione,

17aα-methyl-D-homo-4,16-pregnadiene-3,20-dione,

6α-chloro-17aα-methyl-D-homo-1,4,16-pregnatriene-3,20-dione,

6α-fluoro-17aα-methyl-D-homo-1,4,16-pregnatriene-3,20-dione,

6α, 17aα-dimethyl-D-homo-1,4,16-pregnatriene-3,20-dione,

17aα-methyl-D-homo-1,4,16-pregnatriene-3,20-dione, 6-chloro-17aα-methyl-D-homo-4,6,16-pregnatriene-3,20-dione, 6-fluoro-17aα-methyl-D-homo-4,6,16-pregnatriene-3,20-dione, 6,17aα-dimethyl-D-homo-4,6,16-pregnatriene-3,20-dione, 17aα-methyl-D-homo-4,6,16-pregnatriene-3,20-dione, 6-chloro-17aα-methyl-D-homo-1,4,6,16-pregnatetraene-3,20-dione, 6-fluoro-17aα-methyl-D-homo-1,4,6,16-pregnatetraene-3,20-dione, 6,17aα-dimethyl-D-homo-1,4,6,16-pregnatetraene-3,20-dione, 17aα-methyl-D-homo-1,4,6,16-pregnatetraene-3,20-dione, 6α-chloro-17aα-methyl-1α, 2α-methylene-D-homo-4,16-pregnadiene-3,20-dione, 6α-fluoro-17aα-methyl-1α, 2α-methylene-D-homo-4,16-pregnadiene-3,20-dione, 6α, 17aα-dimethyl-1α, 2α-methylene-D-homo-4,16-pregnadiene-3,20-dione, 17aα-methyl-1 2α-methylene-D-homo-4,6,16-pregnadiene-3,20-dione, 6-chloro-17aα-methyl-1α, 2α-methylene-D-homo-4,6,16-pregnatriene-3,20-dione, 6-fluoro-17aα-methyl-1α, 2α-methylene-D-homo-4,6,16-pregnatriene-3,20-dione, 6,17aα-dimethyl-1α, 2α-methylene-D-homo-4,6,16-pregnatriene-3,20-dione, 17aα-methyl-1α, 2α-methylene-D-homo-4,6,16-pregnatriene-3,20-dione, 17aα-methyl-D-homo-19-norpregna-4,16-diene-3,20-dione, 17aα-ethyl-D-homo-19-norpregna-4,16-diene-3,20-dione and 17aα-methoxy-D-homo-19-norpregna-4,16-diene-3,20-dione.

The D-homosteroids used as starting materials in the foregoing process can be prepared, insofar as their preparation has not yet been described, in analogy to the methods given in the Examples.

D-homosteroids of formula IX in which $R^5$ represents a hydroxy group can be prepared by converting a corresponding 3-keto-$\Delta^4$-D-homosteroid into a 3,3-ethylene ketal, epoxidising this ketal with a peracid (e.g. m-chloroperbenzoic acid), separating the 5α, 6α-epoxide from the product by chromatography, opening the epoxide by treatment with a hydrogen halide (e.g. hydrogen fluoride) in order to introduce a halogen atom into the 6-position or with a methyl-Grignard compound in order to introduce the methyl group into the 6-position and finally hydrolysing the 3-ketal group. D-homosteroids of formula IX in which $R^5$ represents a halogen atom can be prepared by converting a corresponding 3-keto-$\Delta^4$-D-homosteroid into a 3,3-ethylene ketal and treating this ketal with chlorine or bromine fluoride.

A 17a-methyl group can be introduced into a D-homosteroid of the general formula

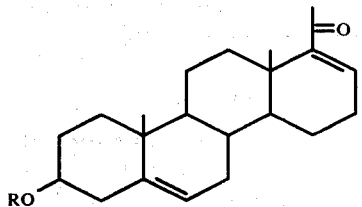

wherein R represents a group such as a tetrahydropyranyl or methoxymethyl group,
in a manner known per se by deprotonation with potassium tert.butylate in a suitable solvent (e.g. tetrahydrofuran or tert.butanol) and subsequent reaction with methyl iodide.

The D-homosteroids of formula I have a hormonal activity, especially on the endocrinal system, and are characterised by a selectivity of action. They can accordingly be used as hormonally active agents (e.g. as progestatives). They can be administered orally or parenterally. Suitable dosages can be from 0.005 mg/kg to 0.15 mg/kg per day.

The D-homosteroids of formula I can be used as medicaments, for example, in the form of pharmaceutical preparations which contain them in association with a compatible pharmaceutical carrier which may be an organic or inorganic inert carrier material suitable for enteral, percutaneous or parenteral administration such as water, gelatine, gum arabic, lactose, starch, magnesium stearate, talc, vegetable oils, polyalkyleneglycols, petroleum jelly etc. The pharmaceutical preparations can be made up in a solid form (e.g. as tablets, dragées, suppositories or capsules), in a semi-solid form (e.g. as salves) or in a liquid form (e.g. as solutions, suspensions or emulsions). The pharmaceutical preparations may be sterilised and/or may contain adjuvants such as preservatives, stabilisers, wetting agents, emulsifiers, salts for varying the osmotic pressure of buffers. The pharmaceutical preparations can also contain therapeutically valuable substances other than the D-homosteroids provided by this invention.

The following Examples illustrate the process provided by the present invention:

EXAMPLE 1

1.15 g of crude 3β-hydroxy-17aα-methyl-D-homo-5,16-pregnadien-20-one are heated to boiling in 22 ml of toluene with 1.1 ml of cyclohexanone and treated with a solution of 550 mg of aluminium isopropylate in 2 ml of toluene. After slow distillation for 45 minutes, the mixture is treated with ether, washed with dilute sulphuric acid and water, dried and evaporated. The residue is chromatographed on silica gel and recyrstallised from methanol. There is obtained 17aα-methyl-D-homo-4,16-pregnadiene-3,20-dione of melting point 181.5°-185.5° C; UV: $\epsilon_{242} = 16100$.

The starting material can be prepared as follows:

10 g of 3β-hydroxy-D-homo-5,17(17a)-pregnadien-20-one are dissolved in 100 ml of tetrahydrofuran and 10 ml of 2,3-dihydro-4H-pyran, treated with 0.1 ml of phosphorus oxychloride and stirred for a further 1 hour at room temperature. The mixture is then stirred into ice-water with the addition of sodium bicarbonate, the separated precipitate is filtered off under suction and rinsed. The residue is taken up in methylene chloride, dried and, after evaporation, recrystallised from diisopropyl ether. There is obtained 3β-(tetrahydropyran-2-yloxy)-D-homo-5,17(17a)-pregnadien-20-one of melting point 153° C/154°-155° C.

1.62 g of potassium tert.butylate are dissolved in 30 ml of absolute tetrahydrofuran and 45 ml of absolute tert.butanol. To the solution cooled in an ice-bath are added under a stream of nitrogen 3.6 g of 3β-(tetrahydropyran-2-yloxy)-D-homo-5,17(17a)-pregnadien-20-one. To this solution, now dark-brown, are added dropwise 1.65 ml of methyl iodide and the mixture is stirred for a further 30 minutes at 0° C and while passing nitrogen over the mixture. The mixture is subsequently stirred into ice-water, the precipitate is filtered off, taken up in methylene chloride, washed with water and dried. The residue obtained after evaporation is chromatographed on silica gel and yields 3β-(tetrahydropyran-2-yloxy)-17aα-methyl-D-homo-5,16-pregnadien-20-one. A sample recrystallised from diisopropyl ether melts at 169.5°-170.5° C.

1.4 g of 3β-(tetrahydropyran-2-yloxy)-17aα-methyl-D-homo-5,16-pregnadien-20-one are treated in 27 ml of methanol with 650 mg of oxalic acid dissolved in 6.5 ml of water and heated to reflux for 1.5 hours. The mixture is then stirred into ice-water, the separated precipitate filtered off under suction, taken up in chloroform and dried. After evaporation, there is obtained crude 3β-hydroxy-17aα-methyl-D-homo-5,16-pregnadien-20-one.

EXAMPLE 2

440 mg of 17aα-acetoxy-3β-hydroxy-D-pregna-5,16-dien-20-one are treated in 30 ml of acetone with 0.55 ml of Jones' reagent, stirred for 5 minutes, poured on to water and extracted with methylene chloride. The methylene chloride solutions are washed with water, dried and evaporated. The resulting oil is stirred for 1 hour at room temperature in 8 ml of dioxane and 0.8 ml of 2-N hydrochloric acid. The mixture is evaporated and the residue chromatographed on silica gel. The resulting 17aα-acetoxy-D-homopregna-4,16-diene-3,20-dione melts at 222°–223° C (from acetone/hexane).

The starting material can be prepared as follows:

3β,17aα-Dihydroxy-D-homopregna-5,16-dien-20-one is reacted in acetic anhydride and triethylamine in the presence of p-N,N-dimethylaminopyridine to give 3β,17aα-diacetoxy-D-homopregna-5,16-dien-20-one [melting point 179°–180° C; $[\alpha]_D = -273°$, c = 0.1% in dioxane ] and this is subsequently partially saponified with potassium carbonate in methanol to give 17aα-acetoxy-3β-hydroxy-D-homopregna-5,16-dien-20-one.

EXAMPLE 3

4.65 g of 17aα-hydroxy-D-homopregna-4,16-diene-3,20-dione and 1.55 g of p-N,N-dimethylaminopyridine are stirred for 16 hours at room temperature under argon in 23.5 ml of triethylamine and 14.5 ml of acetic anhydride. The mixture is poured on to ice-cold dilute hydrochloric acid and extracted with methylene chloride. The methylene chloride solutions are washed neutral with dilute sodium bicarbonate solution and dilute sodium chloride solution, dried and evaporated. Chromatography of the crude product on silica gel and crystallisation twice from acetone/hexane gives 17aα-acetoxy-D-homopregna-4,16-diene-3,20-dione of melting point 223°–224° C; UV: $\epsilon_{240} = 16800$; $[\alpha]_D = -134°$ (c = 0.1% in dioxane).

The starting material can be prepared by oxidising 3β-hydroxy-D-homopregna-5,17-dien-20-one in dimethylformamide and tetrahydrofuran with oxygen in the presence of potassium tert.butylate and trimethyl phosphite to give 3β,17aα-dihydroxy-D-homopregna-5,16-dien-20-one of melting point 241°–243° C; $[\alpha]_D = -187°$ (c = 0.1% in dioxane). By oxidation according to the Pfitzner-Moffatt procedure, there is obtained therefrom 17aα-hydroxy-D-homopregna-4,16-diene-3,20-dione of melting point 177°–178° C; UV: $\epsilon_{240} = 16800$; $[\alpha]_D = +18°$ (c = 0.1% in dioxane).

EXAMPLE 4

450 mg of 17aα,21-dihydroxy-D-homopregna-4,16-diene-3,20-dione and 650 mg of triphenylphosphine are stirred for 1 hour at room temperature under argon in 5 ml of dimethylformamide and 0.5 ml of carbon tetrachloride. The mixture is poured on to dilute sodium chloride solution and extracted with methylene chloride. The methylene chloride extracts are washed with dilute sodium chloride solution, dried over sodium sulphate and evaporated. After chromatography on silica gel, there is obtained 21-chloro-17aα-hydroxy-D-homopregna-4,16-diene-3,20-dione of melting point 243°–245° C (from acetone/hexane); UV: $\epsilon_{240} = 17200$; $[\alpha]_D = +86°$ (c = 0.1% in dioxane).

The starting material can be prepared as follows:

3β,17aα-Dihydroxy-D-homopregna-5,16-dien-20-one in methanol is reacted with iodine in the presence of calcium chloride and calcium oxide to give 3β,17aα-dihydroxy-21,21-diiodo-D-homopregna-5,16-dien-20-one. This is heated together with potassium acetate in acetone, there being obtained 21-acetoxy-3β,17aα-dihydroxy-D-homopregna-5,16-dien-20-one of melting point 175°–176° C (from acetone/hexane); $[\alpha]_D = -81°$ (c = 0.102% in dioxane).

The latter compound is then oxidised in acetone with chromic acid and subsequently isomerised with hydrochloric acid in dioxane to give 21-acetoxy-17aα-hydroxy-D-homopregna-4,16-diene-3,20-dione of melting point 236°–237° C (from acetone/hexane); UV: $\epsilon_{241} = 16700$; $[\alpha]_D = +88°$ (c = 0.1% in dioxane.

By saponification of the last-mentioned compound in methanol with potassium carbonate, there is obtained 17aα,21-dihydroxy-D-homopregna-4,16-diene-3,20-dione of melting point 210°–211° C (from acetone/hexane); $[\alpha]_D = +55°$ (c = 0.107% in dioxane); UV: $\epsilon_{240} = 17000$.

EXAMPLE 5

500 mg of 17aα-acetoxy-6α,7α-epoxy-D-homopregna-4,16-diene-3,20-dione and 1 g of dimethylacetamide hydrochloride are stirred for 70 hours at 40° C in 20 ml of dimethyl sulphoxide. The mixture is poured on to water and extracted with methylene chloride. The methylene chloride extracts are washed with water, dried and evaporated. Chromatography of the residue on silica gel gives 17aα-acetoxy-6-chloro-D-homopregna-4,6,16-triene-3,20-dione of melting point 225°–226° C; $[\alpha]_D = -183°$ (c = 0.1% in dioxane); UV: $\epsilon_{285} = 22300$.

The starting material can be prepared as follows:

3β,17aα-Dihydroxy-D-homopregna-5,16-dione-20-one in dimethylformamide is oxidised with bromine in the presence of lithium bromide and lithium carbonate at 75°–80° C to give 17aα-hydroxy-D-homopregna-4,6,16-triene-3,20-dione (melting point 188°–189° C). Acetylation of this compound yields 17aα-acetoxy-D-homopregna-4,6,16-triene-3,20-dione (melting point 216°–218° C) which, by treatment with p-nitroperbenzoic acid in chloroform, gives 17aα-acetoxy-6α,7α-epoxy-D-homopregna-4,16-diene-3,20-dione (melting point 251°–252° C).

EXAMPLE 6

1.1 g of 17aα-acetoxy-6α,7α-epoxy-D-homopregna-4,16-diene-3,20-dione in 22 ml of acetic acid are stirred with 3.3 g of lithium chloride for 18 hours at room temperature. After precipitation in ice-water, the precipitate is filtered off, taken up in methylene chloride and dried. After evaporation, there is obtained crude 17aα-acetoxy-6β-chloro-7α-hydroxy-D-homopregna-4,16-diene3,20-dione.

1 g of crude 17aα-acetoxy-6β-chloro-7α-hydroxy-D-homopregna-4,16-diene-3,20-dione in 10 ml of pyridine is treated with 1.1 ml of methanesulphonic acid chloride and stirred for 3 hours at room temperature. The mixture is then stirred into ice-water, the precipitate filtered off, taken up in methylene chloride, dried and evaporated. There is obtained crude 17aα-acetoxy-6β-chloro-7α-mesyloxy-D-homopregna-4,16-diene-3,20-dione.

1 g of crude 17aα-acetoxy-6β-chloro-7α-mesyloxy-D-homopregna-4,16-diene-3,20-dione is stirred in 20 ml of dimethylformamide with 5 g of anhydrous sodium acetate for 4 hours at 100° C. After precipitation with ice-water, the precipitate is filtered off, taken up in methylene chloride and dried. After evaporation, the residue is chromatographed on silica gel. There is obtained 17aα-aceotxy-6-chloro-D-homopregna-4,6,16-triene-3,20-dione of melting point 225°–226° C (from acetone/hexane); UV: $\epsilon_{285} = 2300$; $[\alpha]_D = -183°$ (c = 0.1% in dioxane).

EXAMPLE 7

396 mg of 17aα-acetoxy-6-methylene-D-homopregna-4,16-diene-3,20-dione and 80 mg of 5% palladium/-carbon in 2 ml of cyclohexene and 2 ml of benzene are boiled at reflux for 16 hours under argon. The catalyst is filtered off, the filtrate evaporated and the residue chromatographed on silica gel. There is obtained 17aα-acetoxy-6-methyl-D-homopregna-4,6,16-triene-3,20-dione of melting point 222°–223° C; UV: $\epsilon_{289} = 21800$; $[\alpha]_D = -184°$ (c = 0.107% in dioxane).

The starting material can be prepared as follows:

17aα-Acetoxy-D-homopregna-4,16-diene-3,20-dione is reacted in methanol with pyrrolidine with heating. There is obtained 17aα-acetoxy-3-pyrrolidino-D-homopregna-3,5,16-trien-20-one which is reacted with aqueous formaldehyde in alcohol and benzene to give 17aα-acetoxy-6-hydroxymethyl-D-homopregna-4,16-diene-3,20-dione of melting point 224°–226° C (from acetone/hexane).

From this latter compound, by treatment with hydrochloric acid in dioxane, there is obtained 17aα-acetoxy-6-methylene-D-homopregna-4,16-diene-3,20-dione of melting point 211°–213° C (from acetone/hexane); UV: $\epsilon_{261} = 10800$; $[\alpha]_D = -13°$ (c = 0.1% in dioxane).

EXAMPLE 8

396 mg of 17aα-acetoxy-6-methylene-D-homopregna-4,16-diene-3,20-dione and 396 mg of palladium/calcium carbonate are hydrogenated in 39.6 ml of toluene until 1 equivalent of hydrogen has been taken up. The catalyst is filtered off, the filtrate evaporated and the residue stirred in 10 ml of dioxane and 1 ml of 2-N hydrochloric acid for 1 hour at room temperature. The solution is evaporated and the residue purified on a small amount of silica gel. There is obtained 17aα-acetoxy-6α-methyl-D-homopregna-4,16-diene-3,20-dione- of melting point 216°–218° C.

EXAMPLE 9

A solution of 3.2 g of 17aα-acetoxy-6-dibromomethylene-D-homopregna-4,16-diene-3,20-dione in 60 ml of dioxane and 2.5 ml of triethylamine is hydrogenated with 5 g of a 2 percent palladium/-strontium carbonate catalyst until 3 equivalents of hydrogen have been taken up. The catalyst is filtered off and the filtrate acidified to pH 1 with 2-N hydrochloric acid, the 17aα-acetoxy-6β-methyl-D-homopregna-4,16-diene-3,20-dione obtained being isomerised to the corresponding 6α-methyl compound. The mixture is left to stand at room temperature for 2 hours, treated with water and extracted with methylene chloride. The organic extracts are washed neutral with sodium bicarbonate solution and water, dried over sodium sulphate and evaporated in vacuo. The residue is chromatographed on silica gel and the chromatographically uniform fractions are recrystallised from acetone/hexane. There is obtained pure 17aα-acetoxy-6α-methyl-D-homopregna-4,16-diene-3,20-dione of melting point 216°–218° C.

The starting material can be prepared as follows:

17aα-Acetoxy-D-homopregna-4,16-diene-3,20-dione in dioxane is reacted with orthoformic acid methyl ester in the presence of p-toluenesulphonic acid and some methanol to give 17aα-acetoxy-3-methoxy-D-homopregna-3,5,16-trien-20-one of melting point 185°–187° C.

This enol ether is allowed to react in collidine with tetrabromomethane for 80 hours to give 17aα-acetoxy-6-tribromomethyl-D-homopregna-4,16-diene-3,20-dione. The latter is converted into 17a-acetoxy-6-dibromomethylene-D-homopregna-4,16-diene-3,20-dione by heating in pyridine.

EXAMPLE 10 a. 17aα-Acetoxy-D-homopregna-4,16-diene-3,20-dione is converted in ether with acetic anhydride and perchloric acid into 3,17aα-diacetoxy-D-homopregna-3,5,16-trien-20-one and the latter is subsequently reacted in aqueous acetic acid with chlorine in the presence of potassium acetate to give 17aα-acetoxy-6-chloro-D-homopregna-4,16-diene-3,20-dione of melting point 199°–200° C (from ether).

b. 620 mg of 17aα-acetoxy-6-chloro-D-homopregna-4,16-diene-3,20-dione and 30 mg of p-toluenesulphonic acid are left to stand for 18 hours at room temperature in 10 ml of dioxane and 0.6 ml of orthoformic acid ethyl ester. This solution is then added dropwise within 10 minutes to a suspension of 3.0 g of manganese dioxide in 30 ml of glacial acetic acid and 2.4 ml of water and stirred for 60 minutes at room temperature under argon. The mixture is filtered and the filtrate worked-up with water and methylene chloride. After chromatography on silica gel, there is obtained 17aα-acetoxy-6-chloro-D-homopregna-4,6,16-triene-3,20-dione of melting point 225°–226° C (from ether); UV: $\epsilon_{285} = 22300$; $[\alpha]_D = -183°$ (c = 0.1% in dioxane).

EXAMPLE 11

1.35 g of 3β-hydroxy-17aα-ethyl-D-homo-5,16-pregnadien-20-one are heated to boiling in 27 ml of toluene with 1.4 ml of cyclohexane and the mixture is treated with a solution of 650 mg of aluminum isopropylate in 2 ml of toluene. The mixture is then heated for 45 minutes with low distillation, subsequently diluted with ether, washed with 2-N sulphuric acid and water and the residue obtained after evaporation is chromatographed on silica gel. After recrystallisation from diisopropyl ether, there are obtained 485 mg of 17aα-ethyl-D-homo-4,16-pregnadiene-3,20-dione of the melting point 153°–154° C; UV; $\epsilon_{241} = 16800$.

The starting material can be prepared as follows:

1.9 g of potassium tert.butylate are dissolved in 24.5 ml of dimethylformamide and 3.75 ml of tert.butanol. 3.0 g of 3α-(tetrahydropyran-2-yloxy)-D-homo-5,17 (17a)-pregnadien-20-one are dissolved in the solution, which is cooled in an ice-bath, under a stream of nitrogen. 1.38 ml of ethyl iodide are added within 15 minutes and the mixture is then stirred at ice-bath temperature for 40 minutes. The mixture is then stirred into ice-water, the precipitate filtered off, washed well with water and taken up in methylene chloride. After evaporation, the residue is chromatographed on silica gel and, after recrystallisation from methanol, there are obtained 1.8 g of 3β-(tetrahydropyran-2-yloxy)-17aα-ethyl-D-homo-5,16-pregnadien-20-one of melting point 136°–138° C.

1.8 g of 3β-(tetrahydropyran-2-yloxy)-17aα-ethyl-D-homo-5,16-pregnadien-20-one are treated in 36 ml of methanol and 9 ml of water with 300 mg of oxalic acid and the mixture is heated at reflux for 45 minutes. The mixture is then stirred into ice-water, the precipitate filtered off, washed and dried. There are obtained 1.35 g of crude 3β-hydroxy-17aα-ethyl-D-homo-5,16-pregnadien-20-one.

EXAMPLE 12

570 mg of 3β-hydroxy-17aα-butyl-D-homo-5,16-pregnadien-20-one are treated in 11.5 ml of toluene and 0.57 ml of cyclohexanone with a solution of 280 mg of aluminium isopropylate in 1 ml of toluene and the resulting mixture is reacted and worked-up in the manner described in Example 11. After chromatography on silica gel, there are obtained 355 mg of 17aα-butyl-D-homo-4,16-pregnadiene-3,20-dione of melting point 82°–85° C; UV: $\epsilon_{241}$ = 15600.

The starting material can be prepared as follows:

2.5 g of potassium tert.butylate are dissolved in 40 ml of dimethylformamide and 8 ml of tert.butanol. 2.5 g of 3β-(tetrahydropyran-2-yloxy)-D-homo-5,17(17a)-pregnadien-20-one are dissolved in the solution, which is cooled in an ice-bath, under a stream of nitrogen. 1.25 ml of 1-bromobutane are then added dropwise within 15 minutes and the mixture is stirred at ice-bath temperature for 2.5 hours. The mixture is worked-up and the residue chromatographed on silica gel, there being obtained 780 mg of crude 3β-(tetrahydropyran-2-yloxy)-17aα-butyl-D-homo-5,16-pregnadien-20-one. A sample recrystallised from methanol melts at 139°–140° C.

750 mg of crude 3β-(tetrahydropyran-2-yloxy)-17aα-butyl-D-homo-5,16-pregnadien-20-one are reacted in 15 ml of methanol and 3.75 ml of water with 375 mg of oxalic acid in the manner described in Example 11. The mixture is worked-up as described in Example 11 and there are obtained 570 mg of crude 3β-hydroxy-17aα-butyl-D-homo-5,16-pregnadien-20-one.

EXAMPLE 13

4.5 g of 17aα-methyl-D-homo-4,16-pregnadien-3,20-dione are heated at reflux in 90 ml of tert.butanol with 5.4 g of chloranil for 18 hours while stirring. The mixture is then concentrated extensively in a vacuum, the residue taken up in ether, filtered off from unreacted chloranil and the filtrate washed with sodium hydrogen carbonate solution and water. The residue obtained after evaporation is chromatographed on silica gel and, after recrystallisation from diisopropyl ether/acetone, there are obtained 2.25 g of 17aα-methyl-D-homo-4,6,16-pregnatriene-3,20-dione of melting point 180°–181.5° C. UV: $\epsilon_{284}$ = 26900.

EXAMPLE 14

1.5 g of 17aα-methyl-D-homo-4,6,16-pregnatriene-3,20-dione are reacted in 20 ml of tert.butanol and 10 ml of methylene chloride with 1.8 g of 80% 4-nitroperbenzoic acid at room temperature for 18 hours. The mixture is then extensively concentrated in a vacuum, the residue taken up in ether and washed successively with sodium hydrogen sulphite solution, sodium hydrogen carbonate solution and water. The residue obtained after evaporation is chromatographed on silica gel and, after recrystallisation from diisopropyl ether/acetate, yields 475 mg of 6α,7α-epoxy-17aα-methyl-D-homo-4,16-pregnadiene-3,20-dione of melting point 212°–214° C: UV: $\epsilon_{240}$ = 14600.

1.4 g of 6α,7α-epoxy-17aα-methyl-D-homo-4,16-pregnadiene-3,20-dione are saturated in 28 ml of acetic acid while cooling with dry hydrogen chloride gas. After standing for hours at room temperature, the mixture is stirred into ice-water and the precipitate which forms is filtered off and taken up in ether. The ether phase is washed with sodium hydrogen carbonate solution and water and the residue obtained after evaporation is chromatographed on silica gel. After recrystallisation from diisopropyl ether/acetone, there are obtained 1.03 g of 6-chloro-17aα-methyl-D-homo-4,6,16-pregnatriene-3,20-dione of melting point 178.5°–179.5° C: UV: $\epsilon_{286}$ =22100.

EXAMPLE 15

10.0 g of 17aα-methyl-D-homo-4,16-pregnadiene-3,20-dione are heated at reflux for 18 hours in 200 ml of dioxane with 20 g of 2,3-dichloro-5,6-dicyano-benzoquinone and 1 g of p-toluenesulphonic acid. The mixture is then extensively concentrated in a vacuum, the residue taken up in ether, filtered off from undissolved hydroquinone and the filtrate washed with sodium hydrogen carbonate solution and water. The residue obtained after evaporation is chromatographed on silica gel. After recrystallisation from diisopropyl ether/acetone, there are obtained 5.6 g of 17aα-methyl-D-homo-1,4,6,16-pregnatetraene-3,20-dione of melting point 172°–174.5° C: UV: $\epsilon_{223}$ = 11700, $\epsilon_{253}$ =9880, $\epsilon_{300}$ = 11100.

EXAMPLE 16

6.07 g of trimethylsulphoxonium iodide are treated in 138 ml of dimethyl sulphoxide with 992 mg of sodium hydroxide and the mixture is stirred at room temperature for 1 hour. 4.65 g of 17aα-methyl-D-homo-1,4,6,16-pregnatetraene-3,20-dione are then added and stirring at room temperature is continued for 4 hours. After precipitation with ice-water, the precipitate is filtered off, taken up in ether, washed with water, dried and evaporated. The residue is recrystallised from diisopropyl ether/acetone and there are obtained 3.9 g of 17aα-methyl-1α,2α-methylene-D-homo-4,6,16-pregnatriene-3,20-dione of melting point 160.5°–167° C: UV: $\epsilon_{283}$ = 19400.

EXAMPLE 17

3.15 g of 17aα-methyl-1α,2α-methylene-D-homo-4,6,16-pregnatriene-3,20-dione are treated in 63 ml of tert.butanol and 31 ml of methyl chloride with 3.78 g of 80% 4-nitroperbenzoic acid and the mixture is stirred at room temperature for 22 hours. The mixture is then worked-up in the manner described in Example 5 and, after chromatography on silica gel and recrystallisation from diisopropyl ether/acetone, there are obtained 1.4 g of 6α,7α-epoxy-17aα-methyl-1α,2α-methylene-D-homo-4,16-pregnadiene-3,20-dione of melting point 164.5°–167° C; UV: $\epsilon_{236}$ = 12200.

1.3 of 6α,7α-epoxy-17aα-methyl-1α,2α-methylene-D-homo-4,16-pregnadiene-3,20-dione are stirred at room temperature for 20 hours in 26 ml of acetic acid with 3.9 g of lithium chloride. The mixture is then stirred into ice-water, the precipitate which separates is filtered off, taken up in ether and the ether phase washed with sodium hydrogen carbonate solution and water. After evaporation, there are obtained 1.6 g of crude 6β-chloro-7α-hydroxy-17aα-methyl-1α,2α-methylene-D-homo-4,16-pregnadiene-3,20-dione.

1.6 g of crude 6β-chloro-7α-hydroxy-17aα-methyl-1,60 ,2α-methylene-D-homo-4,16-pregnadiene-3,20-dione are treated in 16 ml of pyridine with 1.6 ml of methanesulphonic acid chloride and the mixture is then stirred at room temperature for 4.5 hours. The mixture is subsequently stirred into ice-water, the precipitate which separates is filtered off, washed well with water and taken up in methylene chloride. After evaporation, there are obtained 1.9 g of crude 6β-chloro-7α-mesyloxy-17aα-methyl-1α,2α-methylene-D-homo-4,16-pregnadiene-3,20-dione.

1.9 g of crude 6β-chloro-7α-mesyloxy-17aα-methyl-1α,2α-methylene-D-homo-4,16-pregnadiene-3,20-dione are stirred in 38 ml of dimethylformamide with 9.5 g of anhydrous sodium acetate for 4.5 hours at 100° C. The mixture is then stirred into ice-water, the precipitate filtered off, washed with water and taken up in methylene chloride. The residue obtained after evaporation is chromatographed on silica gel and, after recrystallisation from diisopropyl ether/acetone, there are obtained 990 mg of 6-chloro-17aα-methyl-1α,2α-methylene-D-homo-4,6,16-pregnatriene-3,20-dione of melting point 183°–185.5° C: UV: $\epsilon_{283}$ = 17100.

EXAMPLE 18

2.4 g of 17aα-acetoxy-1α,2α-methylene-D-homo-4,6,16-pregnatriene-3,20-dione are treated in 24 ml of methylene chloride and 48 ml of tert.butanol with 3 g of 80 percent 4-nitroperbenzoic acid and the mixture is left to stand at room temperature for 18 hours. The solution is then diluted with ether, washed with sodium sulphite solution, water, sodium hydrogen carbonate solution and water, dried and evaporated. The residue is chromatographed on silica gel and there are obtained, after recrystallisation from diisopropyl ether/acetone, 1.1 g of 17aα-acetoxy-6α,7α-epoxy-1α,2α-methylene-D-homo-4,16-pregnadiene-3,20-dione of melting point 249°–250.5° C (decomposition): UV: $\epsilon_{236}$ = 12100.

1.6 g of 17aα-acetoxy-6α,7α-epoxy-1α,2α-methylene-D-homo-4,16-pregnadiene-3,20-dione are stirred in 32 ml of acetic acid with 5.4 g of lithium chloride for 6 hours at room temperature. The mixture is then stirred into ice-water, the precipitate is filtered off, washed, taken up in methylene chloride, dried and evaporated. The residue is chromatographed on silica gel and there are obtained 1.45 g of 6β-chloro-7α-hydroxy-17aα-acetoxy-1α,2α-methylene-D-homo-4,16-pregnadiene-3,20-dione; UV: $\epsilon_{235}$ = 10700.

1.05 g of 6β-chloro-7α-hydroxy-17aα-acetoxy-1α,-2α-methylene-D-homo-4,16-pregnadiene-3,20-dione are treated in 10 ml of pyridine with 1 ml of methanesulphonic acid chloride and the mixture is stirred at room temperature for 6.5 hours. The mixture is then stirred into ice-water, the precipitate filtered off, washed, taken up in methylene chloride and dried. After evaporation, there are obtained 1.1 g of crude 6β-chloro-7α-mesyloxy-17aα-acetoxy-1α,2α-methylene-D-homo-4,16-pregnadiene-3,20-dione.

1.1 g of crude 6β-chloro-7α-mesyloxy-17aα-acetoxy-1α,2α-methylene-D-homo-4,16-pregnadiene-3,20-dione are stirred for 5 hours at 100° C in 22 ml of dimethylformamide with 5.5 g of anhydrous sodium acetate. The mixture is then stirred into ice-water, the precipitate filtered off, washed and taken up in methylene chloride. After evaporation, the residue is chromatographed on silica gel and there are obtained, after recrystallisation from diisopropyl ether/acetone, 590 mg of 6-chloro-17aα-acetoxy-1α,2α-methylene-D-homo-4,6,16-pregnatriene-3,20-dione of melting point 218°–219° C; UV: $\epsilon_{283}$ = 17400.

EXAMPLE 19

7.6 g of 17aα-hydroxy-D-homo-4,6,16-pregnatriene-3,20-dione are stirred in 190 ml of absolute dioxane for 18 hours at 100° C with 7.6 g of 2,3-dichloro-5,6-dicyano-benzoquinone. The mixture is then filtered off from precipitated hydroquinone, washed well with ether and the filtrate washed with sodium hydrogen carbonate solution and water. After evaporation, the residue is chromatographed on silica gel and there are obtained, after recrystallisation from diisopropyl ether-/acetone, 4.4 g of 17aα-hydroxy-D-homo-1,4,6,16-pregnatetraene-3,20-dione of melting point 196°–198° C; UV: $\epsilon_{222}$ = 12500, $\epsilon_{258}$ = 9420, $\epsilon_{301}$ = 12800.

EXAMPLE 20

4.1 g of trimethylsulphoxonium iodide are reacted in 93 ml of dimethyl sulphoxide with 671 mg of sodium hydroxide to form dimethylsulphoxonium methylide. To this solution are added 3.15 g of 17aα-hydroxy-D-homo-1,4,6,16-pregnatetraene-3,20-dione and the mixture is then stirred at room temperature for 18 hours. The mixture is then stirred into ice-water weakly acidified with acetic acid, the precipitate is filtered off, washed and dried. There are obtained 2 g of crude 17aα-hydroxy-1α,2α-methylene-D-homo-4,6,16-pregnatriene-3,20-dione. A sample recrystallised from diisopropyl ether/acetone melts at 198.5°–200.5° C; UV: $\epsilon_{283}$ = 20000.

EXAMPLE 21

3.3 g of crude 17aα-hydroxy-1α,2α-methylene-D-homo-4,6,16-pregnatriene-3,20-dione are left to stand in 16.7 ml of triethylamine and 10.3 ml of acetic anhydride for 18 hours at 5° C with 1.1 g of 4-dimethylamino-pyridine. The mixture is then stirred into ice-water, the precipitate which forms is filtered off, washed and dried. After chromatography on silica gel and recrystallisation from diisopropyl ether/acetone, there are obtained 2.4 g of 17aα-acetoxy-1α,2α-methylene-D-homo-4,6,16-pregnatriene-3,20-dione of melting point 216°–218° C; UV: $\epsilon_{282}$ = 20500.

EXAMPLE 22

9.0 g of 17aα-methyl-D-homo-4,16-pregnadiene-3,20-dione are heated at reflux while stirring in 135 ml of methanol and 4.86 ml of pyrrolidine. After cooling in an ice-bath, the precipitate which separates is filtered off under suction and dried. There are obtained 9.6 g of 3-pyrrolidino-17aα-methyl-D-homo-3,5,16-pregnatrien-20-one of melting point 184°–196° C (slow decomposition); UV: $\epsilon_{277}$ = 22000.

9.6 g of 3-pyrrolidino-17aα-methyl-D-homo-3,5,16-pregnatrien-20-one are dissolved in 1.35 litres of ethanol and 676 ml of benzene and added dropwise within 10 minutes to 17.7 ml of 40 percent aqueous formaldehyde solution. The resulting mixture is then stirred at room temperature for 1 hour and extensively concentrated in a vacuum. The residue is chromatographed on silica gel and there are obtained 4.1 g of crude 6β-hydroxymethyl-17aα-methyl-D-homo-4,16-pregnadiene-3,20-dione.

4.1 g of crude 6β-hydroxymethyl-17aα-methyl-D-homo-4,16-pregnadiene-3,20-dione are stirred in 275 ml of dioxane for 2 hours at room temperature with 13.25 ml of 5-N hydrochloric acid. The hydrochloric acid is neutralised with excess sodium hydrogen carbonate, the inorganic salts are filtered off and the filtrate is evaporated to dryness in a vacuum. The residue is chromatographed on silica gel and, after recrystallisation from diisopropyl ether/acetone, there are obtained 2.3 g of 17aα-methyl-6-methylene-D-homo-4,16-pregnadiene-3,20-dione of melting point 177°–178° C.

1.0 g of 17aα-methyl-6-methylene-D-homo-4,16-pregnadiene-3,20-dione is heated at reflux for 8 hours in 35 ml of absolute ethanol with 500 mg of anhydrous sodium acetate and 75 mg of 5% palladium/carbon catalyst, 2 ml of a 0.5 percent ethanolic cyclohexene solution being added dropwise each hour. The mixture is filtered off from the catalyst, the filtrate evaporated to dryness in a vacuum, the residue taken up in methylene chloride, washed with water and evaporated. Recrystallisation from diisopropyl ether yields 850 mg of 6,17aα-dimethyl-D-homo-4,6,16-pregnatriene-3,20-dione of melting point 160°–161° C; UV: $\epsilon_{290} = 22600$.

EXAMPLE 23

A solution of 4.9 g of 3,3-ethylenedioxy-17aα-hydroxy-D-homo-19-norpregna-5(10),16-dien-20one in -one 100 ml of methanol is treated with 1.5 ml of concentrated hydrochloric acid in 10 ml of water and the mixture is stirred at 25° C for 18 hours. The mixture is neutralised by the addition of aqueous bicarbonate, freed from methanol on a rotary evaporator and partitioned between dichloromethane and water. The organic phase is washed with water, dried over sodium sulphate and evaporated on a rotary evaporator to yield 5 g of a crude product. From this crude product, after two recrystallisations from dichloromethane/ether, there are obtained 3.4 g of 17aα-hydroxy-D-homo-19-norpregna-4,16-diene-3,20-dione of melting point 219°–220° C; $[\alpha]_{589}^{25} = -41°$ (c = 0.099 in dioxane).

The starting material can be prepared as follows:

76.5 ml of a ca 20–25 percent solution of n-butyllithium in hexane are introduced by stirring at −78° C under argon into a solution of 27.7 ml of N-cyclohexyl-isopropylamine in 100 ml of tetrahydrofuran. 150 ml of this solution are introduced by stirring within 2 hours under argon into a solution, cooled to −78° C, of 20 g of D-homoestrone methyl ether in 100 ml of dichloromethane. After stirring for a further 2 hours at −78° C, the mixture is treated with a solution of 10 g of ammonium chloride in 50 ml of water, the aqueous phase made acid by the addition of 1-N hydrochloric acid and then extracted with dichloromethane. After washing with saturated bicarbonate solution and water and after drying over sodium sulphate, the solution is evaporated to dryness on a rotary evaporator. The crude product obtained is dissolved in 100 ml of toluene and warmed at reflux for 4 hours. The residue obtained after evaporation is adsorbed on 600 g of silica gel (0.06–0.2 mm). Elution with hexane/ethyl acetate (9:1) yields 20.8 g (90%) of 17aα-chloro-3-methoxy-D-homoestra-1,3,5(10)-triene-17aβ-carboxaldehyde of melting point 116°–117° C (from dichloromethane/hexane); $[\alpha]_{589}^{25} = -5°$ (c = 0.101 in dioxane).

A solution of 20.8 g of 17aα-chloro-3-methoxy-D-homoestra-1,3,5(10)-triene-17aβ-carboxaldehyde in 25 ml of hexamethylphosphoric acid triamide is treated with 2.5 g of lithium chloride and stirred at 50° C for 12 hours with the portionwise gradual addition of 5 g of sodium bicarbonate. After standing overnight at 25° C, the mixture is treated with ether, washed three times with water and once with saturated bicarbonate solution, dried over sodium sulphate and concentrated on a rotary evaporator. The residue is adsorbed on 1 kg of silica gel (0.06–0.2 mm). Elution with dichloromethane yields 10.1 g (50%) of 3-methoxy-D-homoestra-1,3,5(10),17-tetraene-17a-carboxaldehyde of melting point 126°–127° C (from acetone/ether); $[\alpha]_{589}^{25} = +207°$ (c = 0.100 in dioxane).

45 ml of a ca 2-M solution of methyllithium in ether are added dropwise at 0° C under argon while stirring to a solution of 18 g of 3-methoxy-D-homoestra-1,3,5(10),17-tetraene-17a-carboxaldehyde in 250 ml of absolute tetrahydrofuran. After 2 hours, the mixture is treated with aqueous ammonium chloride solution and extracted four times with ether. The organic phases are washed twice with soda, dried over sodium sulphate and concentrated on a rotary evaporator. The crude product is dissolved in 400 ml of tert.butanol and 400 ml of tetrahydrofuran and added dropwise to 1.2 litres of anhydrous ammonia. The boiling solution is treated portionwise with 6.1 g of sodium. After 2.5 hours, the ammonia is distilled off, the reaction mixture concentrated on a rotary evaporator and partitioned between ether and water. After drying over sodium sulphate, the solution is concentrated on a rotary evaporator. The evaporation residue is dissolved in 50 ml of dichloromethane, treated with 100 ml of ethyleneglycol and 25 ml of glacial acetic acid and then stirred at 25° C for 18 hours. The mixture is poured on to ice-cold 3-N sodium hydroxide, extracted with ether and, after washing with water and drying over sodium sulphate, concentrated on a rotary evaporator. The crude product obtained is dissolved in 100 ml of pyridine and treated at 0°–5° C with 200 ml of a ca 1-M solution of chromium trioxide in pyridine/water (10:1). After stirring at 25° C for 4 hours, the mixture is treated with 5 ml of ethanol and concentrated on a rotary evaporator. The residue is treated with 500 ml of ether and 300 ml of water and filtered under suction over Speedex. The organic phase of the filtrate is washed with water, dried over sodium sulphate and concentrated on a rotary evaporator. The residue is adsorbed on 500 g of silica gel (0.06–0.2 mm). Elution with dichloromethane containing 0.5–1 percent methanol yields 10.5 g of pure 3,3-ethylenedioxy-D-homo-19-norpregna-5(10),17-dien-20-one of melting point 147°–148° C (from ether/hexane): $[\alpha]_{589}^{25} = +238°$ (c = 0.101 in dioxane).

A solution of 5.5 g of 3,3-ethylenedioxy-D-homo-19-norpregna-5(10),17-dien-20-one in 25 ml of tetrahydrofuran is added dropwise to a mixture of 15 ml of tert.butanol, 25 ml of dimethylformamide and 2.5 ml of trimethylphosphite. The solution is cooled to −25° C, treated with 1.3 g of potassium tert.butylate and vigorously stirred in an oxygen atmosphere. 360 ml of oxygen are consumed within 25 minutes. The mixture is then poured on to ice-water and extracted with ether. After washing with water, drying over sodium sulphate and evaporation on a rotary evaporator, the crude product is combined with 2.3 g of an identical crude product and adsorbed on 250 g of silica gel (0.06–0.2 mm). Elution with hexane/ethyl acetate (4:1) yields 4.18 g of amorphous 3,3-ethylenedioxy-17aα-hydroxy-19-norpregna-5(10),16-dien-20-one.

EXAMPLE 24

A solution of 4 g of 17aα-hydroxy-D-homo-19-nor-pregna-4,16-diene-3,20-dione in 40 ml of acetic anhydride and 40 ml of triethylamine is treated with 0.5 g of 4-dimethylaminopyridine and the mixture is stirred at 25° C. After 24 hours, the mixture is poured on to ice-cold 1-N hydrochloric acid and extracted with ether. After washing twice with water, drying over sodium sulphate and concentration on a rotary evaporator, there are obtained 7 g of a crude product which is adsorbed on 200 g of silica gel. Elution with dichloromethane yields 2.5 g of 17aα-acetoxy-D-homo-19-nor-pregna-4,16-diene-3,20-dione of melting point 210°–212° C (from dichloromethane/ether/hexane): $[\alpha]_{589}^{25} = -196°$ (c = 0.100 in dioxane).

EXAMPLE 25

A solution of 2.5 g of 17aα-hydroxy-D-homo-19-nor-pregna-4,16-diene-3,20-dione in 30 ml of caproic acid anhydride and 30 ml of triethylamine is treated with 0.5 g of 4-dimethylamino-pyridine and the mixture is stirred at 25° C. After 21 hours, the mixture is poured on to ice-cold 1-N hydrochloric acid and extracted with ether. After washing three times with water, drying over sodium sulphate, evaporation on a rotary evaporator and warming in a vacuum (0.1 Torr), there are obtaned 3.3 g of a crude product which is adsorbed on 100 g of silica gel (0.06–0.2 mm). Elution with dichloromethane yields 1.7 g of 17aα-caproyloxy-D-homo-19-norpregna-4,16-diene-3,20-dione; $UV_{max}$ (ethanol): 239/9 nm ($\epsilon$ = 17000).

EXAMPLE 26

500 mg of 17a-acetoxy-6,7 -epoxy-D-homo-pregna-4,16-diene-3,20-dione in 10 ml of urea. 3 HF are stirred for 10 minutes at room temperature. The reaction mixture is then poured into water and extracted with methylene chloride. The methylene chloride solutions are washed with diluted sodium bicarbonate solution and water, dried and evaporated. Chromatography on silica gel using methylene chloride/acetone yields 17a-acetoxy-6β-fluoro-7α-hydroxy-D-homo-pregna-4,16-diene-3,20-dione.

1 g of 17a-acetoxy-6β-fluoro-7α-hydroxy-D-homo-pregna-4,16-diene-3,20-dione are stirred with 10 ml of pyridine and 1.1 ml of methanesulphonyl chloride for 4 hours at room temperature. The reaction mixture is decomposed with ice, poured on 2 N hydrochloric acid and extracted with methylene chloride. The methylene chloride solutions are washed with sodium bicarbonate solution and water until neutral, dried and evaporated. There is obtained 1.1 g of 17a-acetoxy-6β-fluoro-7α-methanesulphonyloxy-D-homo-pregna-4,16-diene-3,20-dione. This compound is dissolved in 20 ml of dimethylformamide and stirred with 5 g of anhydrous sodium acetate for 30 hours at 100°. The reaction mixture is poured into water and the product is extracted with ether. The ethereal solutions are washed twice with brine, dried and evaporated. After chromatography on silica gel there is obtained 17a-acetoxy-6-fluoro-D-homo-pregna-4,6,16-triene-3,20-dione of m.p. 205°–207° (from acetone/hexane).

EXAMPLE 27

A solution of 5.0 g of 17a-hydroxy-D-homo-pregna-4,16-diene-3,20-dione in 25 ml of dimethylformamide and 25 ml of ethyl iodide is stirred with 10 g of freshly prepared silver oxide for 4½ hours at 50°. 140 ml of methylene chloride are then added to the reaction mixture and the silver salt is filtered off. The filtrate is washed four times with water, dried with sodium sulphate and evaporated under reduced pressure. The residue is chromatographed on 400 g of silica gel using hexane-ether (4:1) as the solvent. There is obtained 1.1 g of pure 17a-ethoxy-D-homo-pregna-4,16-diene-3,20-dione. M.p. 183°–185° (from acetone/hexane), UV $\epsilon_{241}$ = 16 000, $[\alpha]_D^{25°}$ = +7° (c = 0.1 in dioxane).

EXAMPLE 28

A mixture of 5.0 g of 21-mesyloxy-17a-hydroxy-D-homopregna-4,16-diene-3,20-dione, 5.0 g of potassium fluoride and 100 ml of dimethylformamide is heated to 100° for 20 hours. The solvent is evaporated under reduced pressure and the residue treated with water and extracted with ether. The ethereal extracts are washed with water several times, dried over sodium sulphate and evaporated. The residue is crystallized from acetone-hexane and yields pure 21-fluoro-17a-hydroxy-D-homo-pregna-4,16-diene-3,20-dione.

The starting material can be prepared as follows:

5.0 g of 17a,21-dihydroxy-D-homo-pregna-4,16-diene-3,20-dione ae dissolved in 50 ml of pyridine. 5.0 ml of methanesulphonyl chloride are added to the solution and the mixture is kept at room temperature for 2 hours, poured into ice water and extracted with methylene chloride-ether. There is obtained almost pure 17a-hydroxy-21-mesylocy-D-homo-pregna-4,16-diene-3,20-dione, which can be directly used in the above reaction.

EXAMPLE 29

1 g of 17a-acetoxy-6-chloro-D-homo-pregna-4,6,16-triene-3,20-dione and 1 g of dichlorodicyanobenzoquinone are heated to reflux in 60 ml of dioxane in a argon atmosphere. After 48 hours, 500 mg of dichlorodicyanobenzoquinone are added and, after a further 10 hours, an additinal 500 mg. After a total of 70 hours the reaction mixture is chromatographed on the 20-fold amount of aluminum oxide II, neutral using methylene chloride-acetone. The crude product is crystallized from acetone-hexane and yields 500 mg of 17a-acetoxy-6-chloro-D-homo-pregna-1,4,6,16-tetranene-3,20-dione. M.p. 198°–200°, $[\alpha]_D$ = −240° (c = 0.1% in dioxane). UV $\epsilon_{229}$ = 11 170; $\epsilon_{258}$ = 10 670; $\epsilon_{298}$ = 11 330.

The following Example illustrates a typical pharmaceutical preparation containing the D-homosteroids provided by the present invention: a

EXAMPLE A

A tablet for oral administration can contain the following ingredients:

| | | |
|---|---|---|
| Active ingredient (e.g. 17aα-acetoxy-D-homopregna-4,6,16-triene-3,20-dione) | 1 | mg |
| Lactose | 60 | mg |
| Starch | 37 | mg |
| Talc | 1.8 | mg |
| Magnesium stearate | 0.2 | mg |
| Total weight | 100.0 | mg |

We claim:

1. A D-homosteroid of the formula

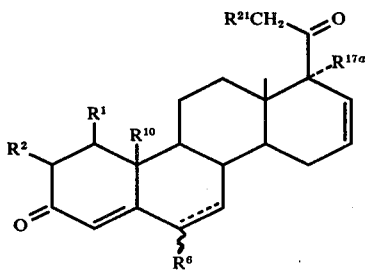

(I)

wherein R¹ and R² each is hydrogen or R¹ and R² together are 1α,2α-methylene or a carbon-carbon bond; R⁶ is hydrogen, fluorine, chlorine or methyl; R¹⁷ᵃ is hydroxy, $C_{1-15}$ hydrocarbon carboxylic acyloxy, alkoxy, or lower alkyl; R¹⁰ is methyl or, when R¹ and R² each is hydrogen, R¹⁰ can also be hydrogen; R²¹ is hydrogen, fluorine or chlorine and the broken line in the 6,7-position is an optional carbon-carbon bond.

2. The compounds of claim 1 wherein R¹, R², R⁶ and R²¹ are hydrogen and R¹⁰ is methyl.

3. The compound of claim 2 which is 17aα-methyl-D-homo-4,16-pregnadiene-3,20-dione.

4. The compound of claim 2 which is 17aα-acetoxy-D-homopregna-4,16-diene-3,20-dione.

5. The compound of claim 2 which is 17aα-ethyl-D-homo-4,16-pregnadiene-3,20-dione.

6. The compound of claim 2 which is 17aα-butyl-D-homo-4,16-pregnadiene-3,20-dione.

7. The compound of claim 2 which is 17aα-ethoxy-D-homo-4,16-pregnadiene-3,20-dione.

8. The compound of claim 2 which is 17aα-methyl-D-homo-4,6,16-pregnatriene-3,20-dione.

9. The compound of claim 1 which is 17aα-methyl-D-homo-1,4,6,16-pregnatetraene-3,20-dione.

10. The compound of claim 1 which is 17aα-hydroxy-D-homo-1,4,6,16pregnatetraene 3,20-dione.

11. The compounds of claim 1 wherein R¹, R², R⁶, R¹⁰ and R²¹ are hydrogen.

12. The compound of claim 11 which is 17aα-hydroxy-D-homo-19norpregna-4,16-diene-3,20-dione.

13. The compound of claim 11 which is 17aα-acetoxy-D-homo-19-norpregna-4,16-diene-3,20-dione.

14. The compound of claim 11 which is 17aα-caproyloxy-D-homo-19-norpregna-4,16-diene-3,20-dione.

15. The compounds of claim 1 wherein R¹, R² and R⁶ are hydrogen, R¹⁰ is methyl and R²¹ is chloro.

16. The compound of claim 15 which is 21-chloro-17aα-hydroxy-D-homopregna-4,16-diene-3,20-dione.

17. The compound of claim 1 wherein R¹, R² and R²¹ are hydrogen, R⁶ is chloro and R¹⁰ is methyl.

18. The compound of claim 17 which is 17aα-acetoxy-6-acetoxy-6-chloro-D-homopregna-4,6,16-triene-3,20-dione.

19. The compound of claim 17 which is 17aα-acetoxy-6-chloro-D-homopregna-4,16-diene-3,20-dione.

20. The compound of claim 17 which is 6-chloro-17aα-methyl-D-homo-4,6,16-pregnatriene-3,20-dione.

21. The compound of claim 1 which is 17aα-acetoxy-6-chloro-D-homo-1,4,6,16-pregnatetranene-3,20-dione.

22. The compounds of claim 1 wherein R¹, R² and R²¹ are hydrogen and R⁶ and R¹⁰ are methyl.

23. The compound of claim 22 which is 17aα-acetoxy-6-methyl-D-homopregna-4,6,16-triene-3,20-dione.

24. The compound of claim 22 which is 17aα-acetoxy-6α-methyl-D-homopregna-4,16-diene-3,20-dione.

25. The compound of claim 22 which is 6,17aα-dimethyl-D-homo-4,6,16-pregnatriene-3,20-dione.

26. The compounds of claim 1 wherein R¹ and R² taken together are methylene.

27. The compound of claim 26 which is 17aα-methyl-1α, 2α-methylene-D-homo-4,6,16-pregnatriene-3,20-dione.

28. The compound of claim 26 which is 6-chloro-17aα-methyl-1α, 2-α-methylene-D-homo-4,6,16-pregnatriene-3,20-dione.

29. The compound of claim 26 which is 6-chloro-17aα-acetoxy-1α, 2-α-methylene-D-homo-4,6,16-pregnatriene-3,20-dione.

30. The compound of claim 26 which is 17aα-hydroxy-1α, 2-α-methylene-D-homo-4,6,16-pregnatriene-3,20-dione.

31. The compound of claim 26 which is 17aα-acetoxy-1α, 2α-methylene-D-homo-4,6,16-pregnatriene-3,20-dione 32. The compounds of claim 1 wherein R¹, R² and R²¹ are hydrogen, R⁶ is fluoro and R¹⁰ is methyl.

33. The compound of claim 32 which is 17aα-acetoxy-6-fluoro-D-homo-pregna-4,6,16-triene-3,20-dione.

34. The compounds of claim 1, wherein R¹, R² and R⁶ are hydrogen, R¹⁰ is methyl and R²¹ is fluoro.

35. The compound of claim 34 which is 21-fluoro-17aα-hydroxy-D-homo-pregna-4,16-diene-3,20-dione.

* * * * *